United States Patent [19]

Willis

[11] 4,017,633
[45] Apr. 12, 1977

[54] SUBSTITUTED 3-(1-AMINOETHYLIDENE)-5-CINNAMOYL-2H-PYRAN-2,6(3H)-DIONES

[75] Inventor: Chester Rhodes Willis, Kingston, Jamaica

[73] Assignee: SmithKline Corporation, Philadelphia, Pa.

[22] Filed: Feb. 18, 1976

[21] Appl. No.: 658,983

Related U.S. Application Data

[63] Continuation-in-part of Ser. No. 511,152, Oct. 2, 1974, abandoned.

[30] Foreign Application Priority Data

Sept. 11, 1975 United Kingdom ............ 37417/75

[52] U.S. Cl. .......................... 424/283; 260/240 J; 260/240 K; 424/279
[51] Int. Cl.$^2$ ...................................... C07D 309/10
[58] Field of Search ................. 260/240 J, 240 K; 424/283, 279

[56] References Cited

UNITED STATES PATENTS

| | | | |
|---|---|---|---|
| 3,558,658 | 1/1971 | McIntyre | 260/240 J |
| 3,644,635 | 2/1972 | Tate et al. | 424/283 |
| 3,751,434 | 8/1973 | Lefebure | 424/283 |

OTHER PUBLICATIONS

Wiley et al. *J. Org. Chem.* 21 (1956) pp. 686–688.
Kiang et al. *J. Chem. Soc.* (c) 1971, pp. 2721–2726.

*Primary Examiner*—Arthur P. Demers
*Attorney, Agent, or Firm*—Richard D. Foggio; William H. Edgerton

[57] ABSTRACT

Substituted 3-(1-aminoethylidene)-5-cinnamoyl-2H-pyran-2,6(3H)-diones useful as inhibitors of certain antigen-antibody reactions, particularly in alleviating allergic manifestations such as asthma, are prepared by reaction of a 3-(1-aminoethylidene)-5-acetyl-2H-pyran-2,6(3H)-dione with an appropriately substituted benzaldehyde.

12 Claims, No Drawings

SUBSTITUTED 3-(1-AMINOETHYLIDENE)-5-CINNAMOYL-2H-PYRAN-2,6(3H)-DIONES

This application is a continuation-in-part of application Ser. No. 511,152 filed Oct. 2, 1974, now abandoned.

This invention relates to novel substituted 3-(1-aminoethylidene)-5-cinnamoyl-2H-pyran-2,6(3H)-diones which are useful as inhibitors of certain antigen-antibody reactions and particularly in alleviating allergic manifestations. The compounds of this invention inhibit the release and/or formation of pharmacologically active mediators from effector cells triggered by the interaction of antigen and a specific antibody fixed to the cell surface. Thus the compounds are valuable in the treatment of allergic diseases such as asthma, rhinitis and urticaria.

The compounds of this invention are represented by the following general structural formula:

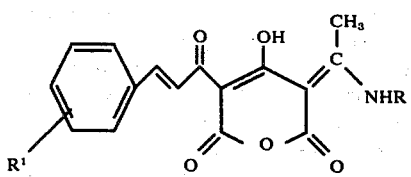

in which:
R represents lower alkyl, straight or branched chain, of from 3 to 6 carbon atoms, phenyl, halophenyl such as chlorophenyl, bromophenyl or fluorophenyl, hydroxyphenyl, methoxyphenyl, p-mercaptophenyl or aminophenyl; and
$R_1$ represents hydrogen, hydroxy, methoxy or dimethoxy.

Preferred compounds of this invention are represented by formula I above when R is hydroxyphenyl or aminophenyl and $R_1$ is hydroxy.

The compounds of this invention are prepared as shown in the following reaction scheme:

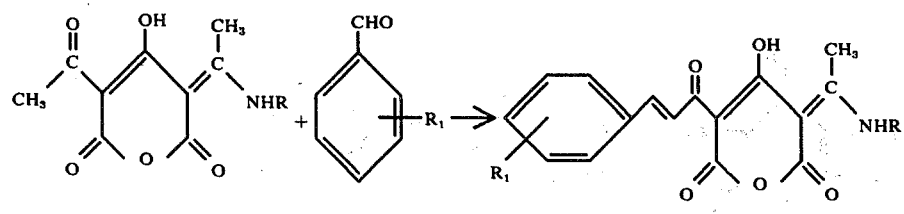

FORMULA II in which R and $R_1$ are as defined in formula I. Thus, a 3-(1-aminoethylidene)-5-acetyl-2H-pyran-2,6(3H)-dione is heated at reflux with a benzaldehyde in an inert organic solvent such as chloroform and in the presence of piperidine for from 4 to 48 hours.

The starting materials of formula II above used herein are generally prepared by reaction of 3,5-diacetyl-4,6-dihydroxy-2H-pyran-2-one with the appropriate amine ($RNH_2$). The reactants are usually heated at reflux in an inert organic solvent such as benzene, toluene or methanol for from two to twelve hours. 3,5-Diacetyl-4,6-dihydroxy-2H-pyran-2-one is obtained by reaction of acetonedicarboxylic acid and acetic anhydride in sulfuric acid at elevated temperature.

The inhibitory activity of the compounds of this invention on mediator release in sensitized tissues is measured by the ability of the active medicament to inhibit the passive cutaneous anaphylaxis (PCA) reaction in rats. In this test system, titered and appropriately diluted serum (from rats previously immunized by the intraperitoneal injection of ovalbuminaluminum hydroxide or ovalbumin-i.m.-*Bordatella pertussis* U.S.P. i.p.-and N. Brasiliensis i.p.) containing reaginic antibodies directed against ovalbumin is injected intradermally at four sites on the shaved backs of normal adult male rats. Forty-eight hours later the animals are injected intravenously with 0.5 ml. of isotonic saline solution containing 5 mg. of the ovalbumin antigen and 5 mg. of Evans blue dye. Chemical mediators such as histamine and serotonin which are released at the sensitized sites as a result of a local cellular anaphylaxis, cause an increase in capillary permeability with resultant leakage of plasma and formation of a wheal. The wheal is visualized by the plasma protein-bound Evans blue dye. Under conditions of the test, the average control wheal is approximately 12 × 12 mm. Thirty minutes following antigen challenge, the animals are killed, the dorsal skin is reflected and the diameter of the wheals recorded. A test compound is administered intravenously, initially at 0.5 minutes prior to antigen challenge (longer pretreatment times and other routes of drug administration, i.e., oral or intraperitoneal may be employed). Percent inhibition is calculated from the difference in mean average wheal diameter between a treated group and saline or appropriate diluent controls.

The compounds of this invention administered intravenously to rats at doses of from 0.5 to 10 mg/kg produce marked inhibition of the PCA reaction. A preferred compound, 5-(m-hydroxycinnamoyl)-4-hydroxy-3-[1-(o-hydroxy-phenylamino)ethylidene]-2H-pyran-2,6(3H)-dione, produced 82% inhibition of the rat PCA wheal at 1.5 mg/kg, i.v. Another preferred compound, 5-(m-hydroxycinnamoyl)-4-hydroxy-3-[1-(o-aminophenylamino)ethylidene]-2H-pyran-2,6(3H)-dione, produced 65% inhibition of the rat PCA wheal at 0.5 mg/kg, i.v. In testing for mechanism of action, the compounds of this invention were found not to provide comparable inhibition of wheals of equal severity produced in rats by the intracutaneous administration of histamine and serotonin following i.v. administration of the test compound at the same dose and pretreatment time which exhibited significant inhibition of the rat 48-hour PCA reaction.

Upon oral administration, 5-(m-hydroxycinnamoyl)-4-hydroxy-3-[1-(o-hydroxyphenylamino)ethylidene]-2H-pyran-2,6(3H)-dione produced 46% inhibition in the rat 48-hour PCA system at 25 mg/kg and a pretreatment time of 15 minutes. Similarly, 5-(m-hydroxycinnamoyl)-4-hydroxy-3-[1-(o-aminophenylamino)e- thylidene]-2H-pyran-2,6(3H)-dione upon oral administration of 25 mg/kg produced 35% inhibition in the rat 48-hour PCA system at a pretreatment time of 15 minutes.

Another feature of this invention is a pharmaceutical composition comprising an appropriate amount of a substituted pyran dione as set forth in formula I in association with a pharmaceutical carrier or diluent. The nature of the composition and the pharmaceutical carrier or diluent will of course depend upon the intended route of administration, i.e., orally, parenterally or by inhalation. Preferably a compound is administered to an animal in a composition comprising an amount sufficient to produce an inhibition of the consequences of the antigen-antibody reaction. When employed in this manner, the dosage of composition is preferably such that from 5 mg. to 500 mg. of active ingredient are administered at each administration. Advantageously equal doses will be administered 1 to 4 times daily with the daily dosage regimen being about 5 mg. to about 2000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g., lactose, for administration from a powder inhalation device. In the above compositions, the amount of carrier or diluent will vary but preferably will be the major proportion of a suspension or solution of the active ingredient. When the diluent is a solid, it may be present in less, equal or greater amounts than the solid active ingredient.

A wide variety of other pharmaceutical forms can be employed. Thus, if a solid carrier is used the preparation can be tableted, placed in a hard gelatin capsule in powder or pellet form, or in the form of a troche or lozenge for oral administration. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

The invention also includes a method of inhibiting the effects of the antigen-antibody reaction which comprises the prior application to the area of the antigen-antibody mechanism a therapeutically effective amount of a substituted pyran dione as defined in formula I. A particular application of the invention is a method of relieving or preventing allergic airway obstruction which comprises administering to an animal a therapeutically effective amount at suitable intervals.

The pharmaceutical preparations are made following the conventional technique of the pharmaceutical chemist involving mixing, granulating and compressing when necessary, or variously mixing and dissolving the ingredients as appropriate to the desired end product.

The accompanying examples illustrate the preparation of compounds of formula I and their incorporation into pharmaceutical compositions of this invention and as such are not to be considered as limiting the invention set forth in the claims appended hereto.

Kiang, A. K. et al. *J. Chem. Soc.* (c) pp. 2721–6 (1971) have questioned the structure assigned by previous authors such as Wiley, R. H. et al. *J. Org. Chem.* 21:686–688 (1956) to the reaction product of acetonedicarboxylic acid and acetic anhydride, designated 5-carboxydehydroacetic acid, and the carbamyl derivatives thereof. Thus, Kiang et al. supra reported that the reaction of acetonedicarboxylic acid with acetic anhydride gave the compound of structure III and that the latter reacted with aniline to form the compound of structure IV:

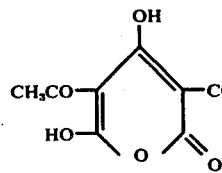

FORMULA III

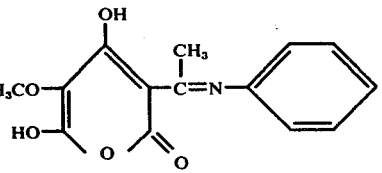

FORMULA IV

Upon investigation which has included $^{13}C$ nuclear magnetic resonance spectral and X-ray crystallographic studies, I have concluded that the reaction of acetonedicarboxylic acid with acetic anhydride gives a product having the tautomeric structure as shown below:

Ⓐ 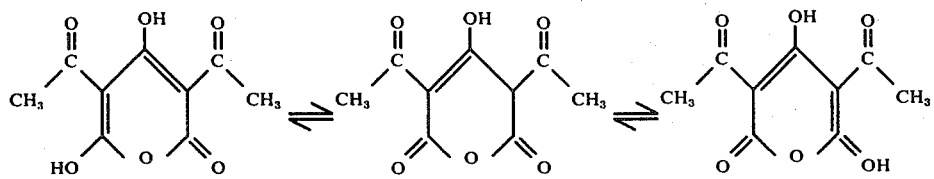

For convenience this product is designated herein as 3,5-diacetyl-4,6-dihydroxy-2H-pyran-2-one. This agrees with Kiang et al's gross structure indicated by formula III above. The rate of tautomerization represented by Ⓐ above is affected, among other factors, by the solvent used in the $^{13}$C spectral study. Accordingly the reaction of this product with an amine, $RNH_2$, gives a product having the tautomeric structures as shown below:

Ⓑ 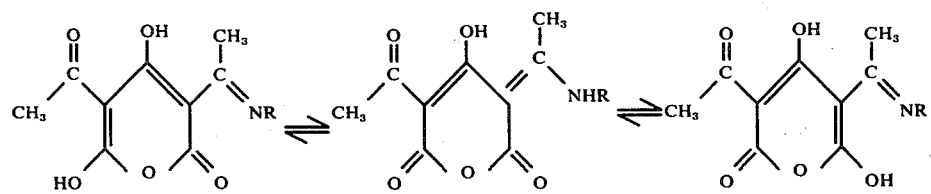

in which R is as defined above for formula I. This also agrees with Kiang et al's gross structure indicated by formula IV above.

Although the exact tautomer represented by Ⓑ in solution has not been identified by $^{13}$C nmr, an X-ray crystallographic study in solid form of the compound wherein R is p-hydroxyphenyl showed that because of extensive conjugation the carbon-carbon bonds throughout the molecule are hybridized and therefore the bond lengths lie somewhere between the values for double and single bonds. However, since one of the exchangeable hydrogens in this compound is located on the nitrogen, for convenience one tautomeric form has been chosen, namely the intermediate enamine pyran-2,6-dione structure, to represent all of the compounds formed by reaction of Ⓐ with an amine, $RNH_2$, as indicated by formula II above.

It will be apparent therefore to one skilled in the art that the more complete representation of the compounds of formula I is shown by the following tautomerization:

EXAMPLE 1

To a boiling solution of 4.24 g. (0.02 m.) of 3,5-diacetyl-4,6-dihydroxy-2H-pyran-2-one in 200 ml. of methanol is added 2.18 g. (0.02 m.) of o-hydroxyaniline. The resulting mixture is refluxed overnight and filtered to yield 5-acetyl-4-hydroxy-3-[1-(o-hydroxyphenylamino)ethylidene]-2H-pyran-2,6(3H)-dione, m.p. 210°–212° C.

A solution of the above prepared pyran dione (0.606 g.) and 0.244 g. of m-hydroxybenzaldehyde in 150 ml. of chloroform is treated with 4 drops of piperidine and refluxed for about 4 hours. The reaction mixture is cooled and washed with 50 ml. of 1N hydrochloric acid and 50 ml. of water. The dried solution is evaporated to give 5-(m-hydroxycinnamoyl)-4-hydroxy-3-[1-(o-hydroxyphenylamino)-ethylidene]-2H-pyran-2,6(3H)-dione, m.p. 180°–182° C. (dec.).

Similarly, a solution of the above pyran dione (2.42 g.) and p-hydroxybenzaldehyde (0.876 g.) in 150 ml. of chloroform with 16 drops of piperidine is refluxed for five hours to give after workup, 5-(p-hydroxycinnamoyl)-4-hydroxy-3-[1-(o-hydroxyphenylamino)ethylidene]-2H-pyran-2,6(3H)-dione, m.p. 257°–260° C.

EXAMPLE 2

A solution of 1.2 g. (0.004 m.) of 5-acetyl-4-hydroxy-3-[1-(o-hydroxyphenylamino)ethylidene]-2H-pyran-2,6(3H)-dione, 0.664 g. (0.004 m.) of 2,3-dimethoxybenzaldehyde in 150 ml. of chloroform and 6 drops of Ⓒ 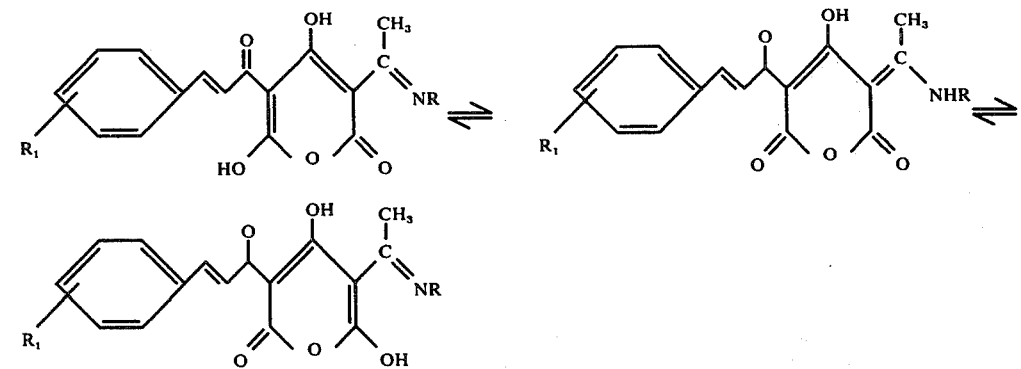

piperidine is refluxed for 1 hours. The solvent is removed from the reaction mixture and the residue is dissolved in a minimum of chloroform. Enough petroleum-ether is added to precipitate the product, 5-(2,3-dimethoxycinnamoyl)-4-hydroxy-3-[1-(o-hydroxyphenylamino)ethylidene]-2H-pyran-2,6(3H)-dione, m.p. 176°–180° C.

EXAMPLE 3

To a boiling solution of 4.2 g. (0.02 m.) of 3,5-diacetyl-4,6-dihydroxy-2H-pyran-2-one in 150 ml. of benzene/methanol is added 1.2 g. (0.02 m.). of n-propylamine and the resulting mixture is refluxed overnight. The reaction mixture is concentrated, filtered and the solid treated with water to give pure 5-acetyl-4-hydroxy-3-[1-(n-propylamino)-ethylidene]-2H-pyran-2,6(3H)-dione, m.p. 145°–148° C.

A mixture of 1.0 g. (0.004 m.) of the above prepared pyran dione and 0.664 g. (0.004 m.) of 2,3-dimethoxybenzaldehyde in 200 ml. of chloroform and 6 drops of piperidine is refluxed for 2 days. The reaction mixture is concentrated and the residue is triturated with ether to furnish 5-(2,3-dimethoxycinnamoyl)-4-hydroxy-3-[1-(n-propylamino)ehtylidene]-2H-pyran-2,6(3H)-dione, m.p. 180°–185° C.

EXAMPLE 4 o-Phenylenediamine (2.1 g., 0.02 m.) is added to a hot solution of 4.2 g. (0.02 m.) of 3,5-diacetyl-4,6-dihydroxy-2H-pyran-2-one in methanol and the resulting mixture is refluxed for 2 hours. The reaction mixture is cooled and filtered to yield 5-acetyl-3-[1-(o-aminophenylamino)ethylidene]-4-hydroxy-2H-pyran-2,6(3H)-dione, m.p. 179°–181° C.

A mixture of 3.0 g. (0.01 m.) of the above prepared pyran dione, 1.4 g. (0.01 m.) of o-methoxybenzaldehyde, 20 drops of piperidine and 200 ml. of chloroform is refluxed for 2 hours. The reaction mixture is concentrated and treated with methanol to give 3-[1-(o-aminophenylamino)ethylidene]-4-hydroxy-5-(o-methoxycinnamoyl)-2H-pyran-2,6(3H)-dione, m.p. 148°–150° C.

Similarly, reaction of an equimolar amount of 2,3-dimethoxybenzaldehyde as described above yields 3-[1-(o-aminophenylamino)ethylidene]-5-(2,3-dimethoxycinnamoyl)-4-hydroxy-2H-pyran-2,6(3H)-dione, m.p. 212°–215° C.

EXAMPLE 5

A mixture of 3.02 g. (0.01 m.) of 5-acetyl-3-[1-(o-aminophenylamino)ethylidene]-4-hydroxy-2H-pyran-2,6(3H)-dione, 1.2 g. (0.01 m.) of m-hydroxy benzaldehyde, 30 drops of piperidine and 250 ml. of chloroform is refluxed for three hours. The resulting solution is concentrated and the residue is dissolved in a small volume of chloroform. Ether is added just until a precipitate is formed and the mixture is allowed to stand overnight at room temperature. Filtration gives the product, 3-[1-(o-aminophenylamino)-ethylidene]-4-hydroxy-5-(m-hydroxycinnamoyl)-2H-pyran-2,6(3H)-dione, m.p. 245°–247° C.

Similarly, reaction with an equimolar amount of p-hydroxybenzaldehyde as described above furnishes the corresponding 3-[1-(o-aminophenylamino)ethylidene]-4-hydroxy-5-(p-hydroxycinnamoyl)-2H-pyran-2,6(3H)-dione, m.p. 223°–225° C.

EXAMPLE 6

3,5-Diacetyl-4,6-dihydroxy-2H-pyran-2-one (5.3 g.) is dissolved in 200 ml. of boiling toluene and an equimolar amount of p-chloroaniline is added. The mixture is refluxed for 12 hours, cooled and filtered to yield 5-acetyl-3-[1-(p-chlorophenylamino)ethylidene]-4-hydroxy-2H-pyran-2,6(3H)-dione, m.p. 205°–206° C.

Following the procedure of Example 1, equimolar amounts of the above pyran dione and benzaldehyde in chloroform with piperidine are reacted to give 3-[1-(p-chlorophenylamino)ethylidene]-5-cinnamoyl-4-hydroxy-2H-pyran-2,6(3H)-dione.

EXAMPLE 7

A mixture of 2.12 g. of 3,5-diacetyl-4,6-dihydroxy-2H-pyran-2-one, 1.25 g. of p-aminothiophenol and 75 ml. of methanol is refluxed for 2 hours, cooled and filtered to yield 5-acetyl-4-hydroxy-3-[1-(p-mercaptophenylamino)ethylidene]-2H-pyran-2,6(3H)-dione, m.p. 207°–210° C.

Equimolar amounts of this pyran dione are m-hydroxybenzaldehyde are reacted as described above in chloroform and piperidine to give 5-(m-hydroxycinnamoyl)-4-hydroxy 3-[1-(p-mercaptophenylamino)ethylidene]-2H-pyran-2,6(3H)-dione.

EXAMPLE 8

To a boiling solution of 3.0 g. (0.014 m.) of 3,5-diacetyl-4,6-dihydroxy-2H-pyran-2-one in 25 ml. of benzene is added 1.4 g. (0.015 m.) of aniline and the resulting mixture is refluxed overnight. The reaction mixture is cooled and filtered to give 5-acetyl-4-hydroxy-3-[1-(phenylamino)ethylidene]-2H-pyran-2,6(3H)-dione, m.p. 184°–186° C.

This derivative is reacted with an equimolar amount of p-hydroxybenzaldehyde as described above in chloroform and piperidine to yield 5-(p-hydroxycinnamoyl)-4-hydroxy-3-[1-(phenylamino)ethylidene]-2H-pyran-2,6(3H)-dione.

As a specific embodiment of a useful composition of this invention, an active ingredient such as 3-[1-(o-aminophenylamino)ethylidene]-4-hydroxy-5-(m-hydroxycinnamoyl)-2H-pyran-2,6(3H)-dione is dissolved in sterile water at a concentration of 0.5% and aerosolized from a nebulizer operating at an air flow adjusted to deliver the desired aerosolized weight of drug.

For oral administration, compositions such as those in the following examples can be prepared.

| Ingredients | Mg./Tablet |
| --- | --- |
| 5-(m-Hydroxycinnamoyl)-4-hydroxy-3-[1-(o-hydroxyphenylamino)ethylidene]-2H-pyran-2,6(3H)-dione | 10 |
| Calcium sulfate, dihydrate | 150 |
| Sucrose | 25 |
| Starch | 15 |
| Talc | 5 |
| Stearic acid | 3 |

The sucrose, calcium sulfate and active ingredient are thoroughly mixed and granulated with hot 10% gelatin solution. The wetted mass is passed through a No. 6 mesh screen directly onto drying trays. The granules are dried at 120° F. and passed through a No. 20 mesh screen, mixed with the starch, talc and stearic acid, and compressed into tablets.

EXAMPLE 10

| Ingredients | Mg./Capsule |
|---|---|
| 5-(m-Hydroxycinnamoyl)-4-hydroxy-3[1-(o-hydroxyphenylamino)ethylidene)-2H-pyran-2,6(3H)-dione | 50 |
| Magnesium stearate | 5 |
| Lactose | 350 |

The above ingredients are screened through a No. 40 mesh screen, mixed and filled into No. 0 hard gelatin capsules.

What is claimed is:

1. A chemical compound of the formula:

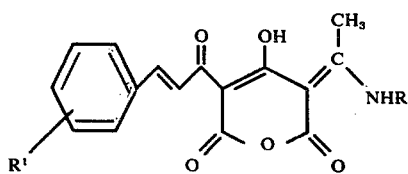

wherein:
R is lower alkyl, straight or branched chain, of from 3 to 6 carbon atoms, phenyl, halophenyl, hydroxyphenyl, methoxyphenyl, p-mercaptophenyl or aminophenyl; and
$R_1$ is hydrogen, hydroxy, methoxy or dimethoxy.

2. A chemical compound according to claim 1 in which R is hydroxyphenyl.

3. A chemical compound according to claim 2 in which $R_1$ is hydroxy.

4. A chemical compound according to claim 3 in which R is o-hydroxyphenyl and $R_1$ is m-hydroxy.

5. A chemical compound according to claim 1 in which R is aminophenyl.

6. A chemical compound according to claim 5 in which R is o-aminophenyl.

7. A chemical compound according to claim 6 in which $R_1$ is m-hydroxy.

8. A chemical compound according to claim 6 in which $R_1$ is p-hydroxy.

9. A chemical compound according to claim 6 in which $R_1$ is o-methoxy.

10. A chemical compound according to claim 6 in which $R_1$ is 2,3-dimethoxy.

11. A pharmaceutical composition for inhibiting the symptons of asthma comprising a nontoxic pharmaceutical carrier or diluent and an amount sufficient to produce said inhibition of a compound of the formula:

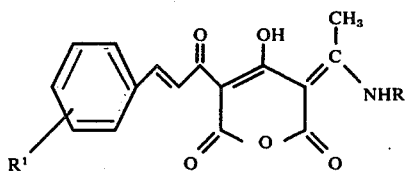

wherein:
R is lower alkyl, straight or branched chain, of from 3 to 6 carbon atoms, phenyl, halophenyl, hydroxyphenyl, methoxyphenyl, p-mercaptophenyl or aminophenyl; and
$R_1$ is hydrogen, hydroxy, methoxy or dimethoxy.

12. The method of inhibiting the symptoms of asthma which comprises administering to an animal in need thereof a therapeutically effective amount for producing said inhibition of a compound of the formula:

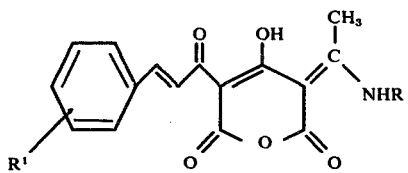

wherein:
R is lower alkyl, straight or branched chain, of from 3 to 6 carbon atoms, phenyl, halophenyl, hydroxyphenyl, methoxyphenyl, p-mercaptophenyl or aminophenyl; and
$R_1$ is hydrogen, hydroxy, methoxy or dimethoxy.

* * * * *